United States Patent [19]

Slettenmark

[11] Patent Number: 5,417,663

[45] Date of Patent: May 23, 1995

[54] APPARATUS FOR CONVEYING LIQUIDS

[75] Inventor: Bruno Slettenmark, Jaerfaella, Sweden

[73] Assignee: Siemens Aktiengesellschaft, Munich, Germany

[21] Appl. No.: 118,592

[22] Filed: Sep. 10, 1993

[30] Foreign Application Priority Data

Sep. 11, 1992 [EP] European Pat. Off. ............ 92115568

[51] Int. Cl.⁶ .................................................. A61M 1/00
[52] U.S. Cl. ................................. 604/126; 604/131; 604/151; 604/123
[58] Field of Search ............... 604/131, 146, 147, 149, 604/151, 118, 126, 123, 122

[56] References Cited

U.S. PATENT DOCUMENTS

| | | | |
|---|---|---|---|
| 3,951,147 | 4/1976 | Tucker et al. | 128/260 |
| 4,198,971 | 4/1980 | Noiles | 604/126 |
| 4,360,019 | 11/1982 | Portner et al. | 604/131 |
| 4,604,090 | 8/1986 | Reinicke | 604/118 |
| 4,627,419 | 12/1986 | Hills | 604/131 |
| 4,684,364 | 8/1987 | Sawyer et al. | 604/123 |
| 4,747,826 | 5/1988 | Sassano | 604/52 |
| 4,808,089 | 2/1989 | Buccholtz et al. | 417/417 |
| 4,842,576 | 6/1989 | Lysaght et al. | 604/131 |
| 4,900,312 | 2/1990 | Nadeau | 604/246 |
| 4,985,015 | 1/1991 | Obermann et al. | 604/67 |
| 5,163,909 | 11/1992 | Stewart | 604/131 |
| 5,211,201 | 5/1993 | Kamen et al. | 137/1 |

*Primary Examiner*—John G. Weiss
*Attorney, Agent, or Firm*—Hill, Steadman & Simpson

[57] ABSTRACT

In a device for conveying liquids having an intermittently energized pump and a filter for retaining air bubbles preceding the input side of the pump, the filter contains an admission opening in the form of a long gap and the gap volume is greater than the conveying volume of the pump given a single pump action. Even an air bubble that nearly completely covers the gap cannot be conveyed therethrough as long as the gap is in contact with the liquid to be pumped at some location.

25 Claims, 1 Drawing Sheet

APPARATUS FOR CONVEYING LIQUIDS

BACKGROUND OF THE INVENTION

1. Field of the Invention

The invention is directed to a device for conveying liquid, particularly to a medication dosing unit.

2. Description of the Prior Art

Medication dosing units generally include an intermittently energized pump and a filter arranged at the input side thereof for retaining air bubbles, the filter being dimensioned such that air bubbles having a larger diameter than a prescribed minimum diameter are prevented from freely passing the filter. Additionally, the maximum pressure drop of the liquid flow produced by the filter given a pump action (stroke) is lower than the pressure required for conveying an air bubble having a larger diameter than the prescribed, minimum diameter through the filter.

Such a device disclosed in U.S. Pat. No. 4,604,090 is a medication dosing unit implantable in a living organism in which an electromagnetically actuatable bellows pump driven by electrical pulses draws a quantity of a liquid medication, corresponding to the working volume of the pump, by suction from a medication reservoir at every pulse. The pump supplies the medication to a catheter that conveys the medication portions to a suitable location in the organism, where the medication is injected. The bellows pump provided in the known apparatus has a relatively large dead volume, so that the medication conveying capacity of the pump decreases with increasing air accumulation when air proceeds into the pump, and the liquid conveying ultimately completely ceases because the quantity of air collected in the pump is merely compressed upon every pump action. A certain quantity of gas is always dissolved in the liquid to be pumped, and air can proceed into the medication reservoir when filling the medication reservoir under normal conditions if complicated countermeasures such as degasification of the liquid or filling the medication reservoir in a vacuum are not undertaken. Therefore, a filter for retaining air bubbles precedes the pump in the known apparatus. The filter is essentially composed of a flexible filter disc in the form of a porous membrane or in the form of a mesh grid having a pore width of 0.22 through 5 $\mu$m, or a mesh width of, for example, 15 $\mu$m, so that only extremely small air bubbles having the same diameter or a smaller diameter can pass the filter unimpeded. Due to the extremely small pore or mesh width of the filter, however, even a slight liquid flow through the filter can cause such a large pressure drop across the filter that larger air bubbles are also forced through the filter. In the known apparatus, the filter disc is fashioned so thinly, and thus so flexibly, that the filter disc is deflected upon every pump action by the suction pressure produced by the pump and then slowly returns to its initial position. As a result, the liquid flow through, and thus the pressure drop across, the filter is limited.

Due to the extremely small pore or mesh width of the filter, there is the risk in the known apparatus that the pores or meshes are very quickly plugged by foreign particles or precipitants of the medication (for example, insulin). As a result—dependent on the flexibility of the filter disc—either the pressure drop as a consequence of the liquid flow through the pore or meshes that are not yet plugged becomes so great that air bubbles are forced through the filter, or the filter no longer returns into its initial position. The flow rate of the pump is diminished under either circumstance. Enlarging the pore or mesh width is precluded, however, because this would lead to an increased air permeability of the filter which must absolutely be avoided because of the aforementioned, relatively large dead volume of the known pump.

When the filter in the known apparatus is partially covered by the accumulating air at its side facing away from the pump, then this leads to the same consequences as in the case of the above-described plugging of the filter pores or meshes. Moreover, the pores or meshes act on the air bubbles like potential troughs wherein the air bubbles adhere and plug the pores or meshes. When the known filter is ultimately completely plugged by air bubbles or is covered by a large air bubble, the liquid conveying entirely ceases.

SUMMARY OF THE INVENTION

In a device for conveying liquid with an intermittently energized pump, it is therefore an object of the invention to effectively prevent the cessation of liquid being conveyed by the pump due to air bubbles in the liquid to be conveyed.

This object is inventively achieved in a liquid conveying device of the type having a bubble-trapping filter at its input side wherein the filter contains an admission aperture or transfer port in the form of a long gap (i.e., long in a direction substantially traverse to the direction of liquid conveyance), the volume of the gap being greater than the conveying volume of the pump in a single pump action. Even when the gap is nearly completely covered by an air bubble, the bubble cannot pass the gap as long as the gap is still in contact with the liquid at any location whatsoever. During a pump action, the air bubble is sucked into the gap without, however, passing completely through the gap because the volume of the gap is greater than the conveying volume of the pump in the pump action. Due to the surface tension of the liquid, the boundary surface between the air bubble and the liquid returns, immediately after the pump action, to its initial position that it had preceding the pump action. The gap then again fills with liquid which proceeds into the gap from that side of the filter facing away from the pump.

This is not possible in a conventional filter having pores or meshes because the pores or meshes are isolated from one another. Assuming that, for example, 99 of 100 pores are covered by air bubbles and that the air bubbles are all uniformly sucked into the pores given a pump action, whereby the overall volume of the air filling the pores then amounts to approximately 99% of the pump volume in the pump action, and the corresponding quantity of 99% of the pump volume would then have to be conveyed through the single, free pore given a refilling of the 99 pores with the liquid. The pressure drop of the flowing liquid thereby arising across this single pore would have to be produced across the other 99 pores due to the surface tension of the air bubbles and this is not possible in the time interval between two pump strokes. Apart therefrom, pores and meshes cannot in practice be manufactured with such precision that they are respectively of exactly the same size over the entire filter. When, due to a partial air cover of exactly a conventional filter, the flow pressure through the uncovered pores therefore becomes so high that it reaches the capillary pressure of the air bubble over the largest air-covered pore, then the air bubbles will be conveyed through this pore since the volume of the pore is only a fraction of the pump volume in a pump action. A pore volume of an individual pore as large as the pump volume, however, cannot be realized since either the pore width (pore) would have be made so large that large air bubbles could also pass unimpeded, or the pore depth would have to become so great that the flow resistance for the liquid and, thus, the pressure drop across the filter, would reach extreme values.

Compared thereto, the gap volume in the apparatus of the invention can be dimensioned larger than the pump volume in a pump action merely by selecting the gap length without having to accept unbeneficial compromises in the dimensioning of the gap width in view of the diameter of the air bubbles to be retained and for the dimensioning of the gap depth in view of the pressure drop generated by the liquid flow. Since it is essentially the gap volume, variable by varying the gap length, which is the determining factor for the retention of air bubbles in the device of the invention, whereas the pore diameter defines the air retention capability of a conventional pore filter because of the extremely small pore volume, the demands for absolute precision in the manufacture of the filter of the invention are far, far lower than given conventional pore or mesh filters.

Finally, the risk of blockage due to particles or precipitates of the liquid is lower given a gap than given a pore or mesh filter. It is particularly insulin solutions and other liquids that contain proteins that tend to adsorption and the formation of surface coats. Since the pressure drop produced by a liquid flow through a filter in a pore filter is dependent on the pore diameter $s_p$ with a factor $s_p^{-4}$ but is dependent on the gap width $s_s$ only with a factor $s_s^{-3}$ given a gap, the flow resistance increases far more rapidly given a constriction of pores than given a constriction of the gap.

In the device of the invention, of course, two or more gaps having the same total length as one single gap can be provided instead of one gap; due to the aforementioned advantages, however, a single gap is preferable. In order to assure in the device of the invention that the boundary surface between the air bubble and the liquid returns to the initial position it had before the pump action after every pump action due to the surface tension of the liquid, so that the gap again fills with liquid, it is preferable that the filter is composed of a material—at least in the environment of the gap—that is wettable by the liquid. One example of this is pure titanium, which has the property of being wetted by insulin dissolved in water as the liquid to be conveyed. Alternatively or in addition, the liquid can have a wetting agent added to it.

In order to prevent the gap from being completely covered by an air bubble insofar as possible, the gap has an optimally broad expanse in a one-dimensional, or preferably two-dimensional, direction. For manufacturing reasons, the gap is preferably fashioned as an annular gap.

In an embodiment of the device of the invention, that side of the filter facing away from the pump, and/or an inside wall of a reservoir accepting the liquid to be pumped and adjoining the liquid, have a shaped portion that prevents an air bubble in the region of the filter from assuming a stable equilibrium position. To that end, the side of the filter facing away from the pump and/or the inside wall of the container adjacent thereto can be essentially convexly fashioned. The risk of a complete air coverage of the gap independently of the arbitrary position of the surface is thus minimum, particularly given an elongated gap extending over a convex surface. As a result, air can collect up to a prescribed amount in the liquid to be conveyed without the filter being capable of being completely covered by the air quantity. When the device of the invention is an implantable medication dosing device, this is fashioned such that the prescribed air quantity is greater by a safety margin than that air quantity that can proceed into the medication reservoir given a normally proceeding filling of the medication reservoir. If the medication reservoir is first emptied before every refilling of the medication reservoir and when the safety margin is selected larger than a residual volume below which a further emptying of the medication reservoir is not technologically possible, then it is precluded in the normal case that the filter will be completely covered by an air bubble.

If the gap of the filter of the invention nonetheless becomes completely covered by an air bubble, liquid is no longer pumped through the filter as soon as this occurs. Dependent on the dimensioning of the filter and of the pump, it can then be provided that either the air bubble is pumped through the filter and through the pump in order to then resume the conveying of the liquid, or that the filter retains the air bubble against the suction pressure of the pump and the liquid conveying thus ceases until the gap of the filter is contacted by the liquid. In order (as in the case, for example, of the infusion of insulin) to be able to first pump the air bubble and then the insulin again through the filter and pump, the pump in the device of the invention is a reciprocating pump having a piston capacity that is free of dead space to the farthest-reaching extent. For example, such reciprocating pumps are disclosed by European Applications 0 259 668 and 0 287 920. These pumps, due to their negligibly small dead space volume, can pump gas bubbles even given a high pressure difference between the inlet side and outlet side of the pump.

When, by contrast, conveying of air is to be completely precluded such as, for example, given infusions into the blood stream, then it is fundamentally adequate to dimension the pump and the gap such relative to one another that the suction pressure produced by the pump is not sufficient for conveying the air bubble covering the gap of the filter through the gap. Since, on the other hand, the suction pressure of the pump should be adequately high in order to suction an air bubble partially covering the gap into the gap and thus to enable liquid conveying as long as the gap is not completely covered by an air bubble, a corresponding dimensioning of the pump is difficult to realize. In a further embodiment of the device of the invention, it is therefore provided that a further filter in the form of a pore and/or mesh filter is arranged between the filter and the pump, the pore or mesh width of this further filter being lower than the width of the gap. The pump and the pore and/or mesh filter can be dimensioned relative to one another dependent on whether an air bubble covering the filter with the gap is to be permitted to be conveyed by the pump. As long as the filter having the gap is not completely covered by an air bubble, the air bubble is retained at the gap and the liquid to be pumped is conveyed through the gap and is subsequently conveyed through the following pore or mesh filter. Only negligibly small air bubbles whose diameter is smaller than the gap width can therefore proceed to the pore or mesh filter.

When the gap is completely covered by an air bubble, air is conveyed through the gap and proceeds to the pore or mesh filter. The air bubble remains clinging to the pore or mesh filter or is eventually conveyed therethrough dependent on the pore or mesh size and on the size of the suction pressure produced by the pump.

The most important difference between the gap filter of the device of the invention and a conventional pore or mesh filter should again be pointed out namely that an air bubble having a larger diameter than the gap width is retained by the gap filter independently of the suction pressure of the pump, as long as the air bubble does not completely cover the whole length of the gap. In a pore or mesh filter, by contrast, a transmission of air occurs as soon as—given a partial coverage of the filter with air—the pressure drop of the liquid flow through the uncovered pores or meshes reaches the capillary pressure of the air bubbles over the pores or meshes covered by them. The device of the invention thus avoids particularly that case wherein, given a certain accumulation of air in front of the filter, a certain air quantity is constantly conveyed by the pump together with the liquid to be pumped. A conveying of liquid free of air bubbles is instead assured in the device of the invention up to the time (if it occurs) that the accumulation of air in front of the filter has become so great that the gap is completely covered along its entire length as a result.

In order to be able to initiate suitable measures if and when the gap is completely covered by air, in a further embodiment of the device of the invention the filter is followed by a monitoring means which detects air bubbles in the liquid conveyed through the filter and/or detects deviations of the pump function from rated values. When the air bubble covering the gap is conveyed through the filter, the air bubble can be detected either directly or indirectly as the function of the pump is modified by the presence of the air bubble. In the infusion of insulin, the patient can be informed of the detection of air either, for example, acoustically or by telemetric transmission to a programming device worn by the patient, so that the patient can inject the insulin with a syringe until the pump again conveys insulin instead of air. Further, the patient can visit a hospital for the emptying and refilling of the medication reservoir. If, by contrast, the pumping of air is to be precluded completely, then the pump can be automatically shut off by the monitoring device. When the air bubble covering the gap cannot be conveyed through the pores due to the low suction pressure of the pump, this likewise leads to modifications of the pump function or even to a standstill of the pump. European Application 0317705 and co-pending U. S. patent application Ser. No. 08/054,146 (Slettenmark, "Dosing Device for the Controlled Delivery of a Liquid") disclose examples of such monitoring devices. For example, the pump energy consumed at every individual pump action can be measured, this being dependent on the conditions in the liquid system preceding and following the pump. The same is true of the pump noise generated by the pump due to cavitation at every pump action or of the traveling time of the piston from its idle position until it reaches the final position, for a pump having an electromagnetically accelerated piston. The presence of air bubbles can also be detected by measuring the light propagation, sound propagation or by measuring electrical parameters in the liquid to be pumped.

DESCRIPTION OF THE DRAWINGS

FIG. 2 shows an exemplary embodiment of the gap filter arrangement of the invention in a side sectional view.

FIG. 3 shows the filter arrangement of FIG. 2 in a view from below.

DESCRIPTION OF THE PREFERRED EMBODIMENTS

Figure 1:
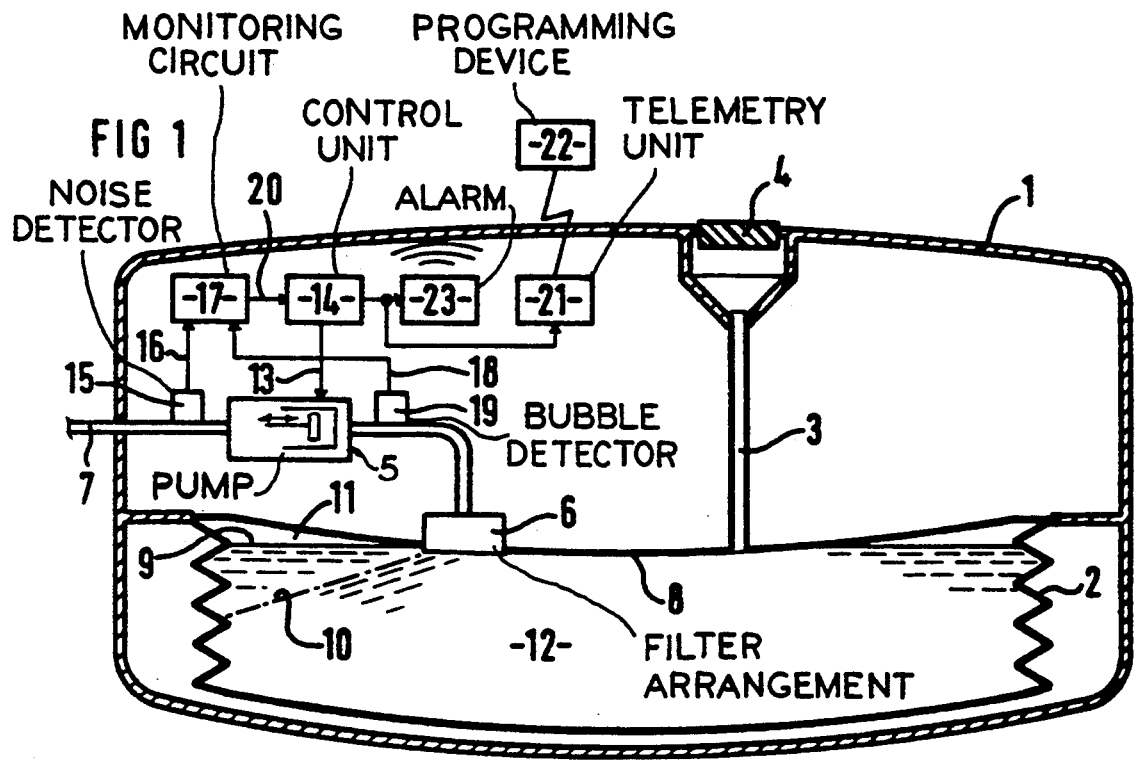
FIG. 1 shows an implantable medication dosing device of the invention in a preferred exemplary embodiment, having a gap filter arrangement for retaining air bubbles.

The implantable medication dosing device shown in FIG. 1 has a housing 1 wherein a medication reservoir 2 is arranged. An admission line 3 has one end connected to the inside of the medication reservoir 2 and its other end terminated by a paracentesis septum 4 let into the wall of the housing 1, and thus sealing the inside of the medication reservoir 2 from the environment of the housing. The housing 1 of the medication dosing device is implanted in the body of a patient in such a way that the paracentesis septum 4 comes to lie just under the skin of the patient, so that a liquid medication, for example insulin, can be filled into the medication reservoir 2 through the skin and through the paracentesis septum 4 lying therebelow with the assistance of a cannula. A medication dosing pump 5 sucks the stored, liquid medication from the reservoir 2 in dosed portions via a filter arrangement 6, and supplies these portions to a catheter 7 that conveys the medication portions to a suitable location in the body of the patient, where the doses are injected.

The filter arrangement 6, whose structure and function are set forth in greater detail below with reference to FIG. 2, serves the purpose of retaining air bubbles that can proceed into the filter arrangement 6 in the form of gases dissolved in the medication, as well as gases collecting as a result of filling the medication reservoir 2 with fresh medication. Since the medication reservoir 2 is first emptied before every refilling—except for a residual volume conditioned by its structure—, a permissible quantity of air proceeding into the medication reservoir 2 together with the medication can be defined for every refilling event on the basis of a suitable shaping of the medication reservoir 2, so that a complete coverage of the filter arrangement 6 with air does not occur regardless of the momentary position of the medication dosing device. To that end, the inside wall 8 of the medication reservoir 2 directly adjoining the filter arrangement is fashioned convexly in the illustrated exemplary embodiment. Boundary surfaces 9 and 10 between a defined air quantity 11 contained in the medication reservoir 2 and the liquid medication 12 are shown for different positions of the medication dosing device. A complete covering of the filter arrangement 6 with air does not occur in either of the two illustrated positions. The significance of this shall be discussed in greater detail below in conjunction with FIG. 2.

The medication dosing pump 5 is an intermittently energized reciprocating pump as disclosed, for example, by in European Applications 0 259 668, 0 287 920 and 0 317 705. Due to the negligibly small dead space, such a reciprocating pump is capable of pumping air bubbles from an under-pressure at the inlet side of the pump 5 to an over-pressure at the outlet of the pump 5. The pump 5 is connected via a control line 13 to a control unit 14 that effects a drive of the pump 5 for every pump action to be executed. A noise sensor 15 is arranged in the region of the output of the pump 5 for monitoring the pump function, this noise sensor 15 being connected via a line 16 to a monitoring circuit 17. An air bubble detector 19 in the form, for example, of a reflection light barrier that is arranged at the inlet side of the pump 5 is also connected to the monitoring circuit 17 via a further line 18. The monitoring circuit 17 evaluates the signals of the noise sensor 15 and of the air bubble detector 19 and conducts them via a control line 20 to the control unit 15, wherein the signals are utilized for the pump control. When an air bubble is detected by the air bubble detector 19 and/or malfunctions of the pump 5 are detected due to changes in the pump noises, the disturbing event is communicated via a telemetry unit 21 to a programming device 22 outside the body of the patient and/or the patient, is directly acoustically informed via an error alarm 23.

FIG. 2 shows a section through the filter arrangement 6 and FIG. 3 shows a view of the filter arrangement 6 at its side facing toward tile medication reservoir 2. The filter arrangement 6 has a filter housing 24 that is open at the side toward the medication reservoir 2, a gap filter 26 and a further filter 27 being arranged therein following one another in the conveying direction 25 of the pump 5. The gap filter 26 is formed by a disc supported in the open side of the housing 24 by a post or pin 32, which extends snugly through the further filter 27. The inside of the filter housing 24 following the further filter 27 is connected via an output line 28 to the inlet side of the pump 5. The gap filter 26 proceeds flush with the inside wall 8 of the medication reservoir 2 at its side 29 facing toward the inside of the medication reservoir 2, and may be convexly curved at that side and has a single admission opening in the form of an annular gap 30. The gap filter 26 is composed of pure titanium, so that it is wetted by the medication liquid 12. The inside wall 8 should also be made of a wettable material. The further filter 27 following the gap filter 26 is fashioned as a pore or mesh filter composed of a material wettable by the liquid 12 as well.

The dimensioning of the gap 30 is based on the following parameters:

| | |
|---|---|
| $Q_{max}$ | maximum liquid flow during a pump action |
| V | conveying volume given a single pump action |
| $\sigma$ | surface tension of the liquid |
| $\eta$ | viscosity of the liquid |
| $\alpha$ | wetting angle of the liquid |
| s | gap width |
| d | gap depth |
| l | gap length |

As shown in FIG. 3, the gap length l is measured along a double-arrowed circular line.

In order to be able to convey an air bubble 31 having a diameter larger than the gap width s through the annular gap 30, a pressure difference $\Delta P_1$ across the gap 30 having $$\Delta P_1 = (2 \cdot \sigma \cdot \cos \alpha)/s$$

is required. Given the maximum liquid flow $Q_{max}$, a pressure drop $\Delta P_2$ of $$\Delta P_2 = 12 \cdot Q_{max} \cdot \eta \cdot d/(l \cdot S^3)$$

arises across the filter 26, whereby $\Delta P_2$ increases when the gap 30 is partially covered with air because the effective, free gap length thereby decreases. As long as $$\Delta P_1 > \Delta P_2$$

applies, no air bubble 31 having a diameter larger than the gap width s can pass the gap 30, so that the following dimensioning rule for the gap 30 is derived therefrom:

$$d/(l \cdot s^2) < (\sigma \cos \alpha)/(6 \cdot \eta \cdot Q_{max}). \tag{1}$$

When the gap 30 is nearly completely covered by the air bubble 31, the free gap length for the passage of liquid becomes so small that $$P_2 > \Delta P_1$$

applies and the air bubble 31 is drawn into the gap 30. In order to prevent the air bubble 31 from passing through the gap 30 in a single pump action, the gap volume is selected greater than the conveying volume V of the pump 5 in one pump action by a factor $k_1 (k_1 > 1)$:

$$l \cdot s \cdot d > k_1 \cdot V \tag{2}$$

Given the condition that the gap 30 is in contact with the liquid 12 in the medication reservoir 2 at some location, the boundary surface between the air bubble 31 and the liquid 12 returns immediately after the pump action to the initial position it had before the pump action due to the surface tension of the liquid 12, causing the gap 30 again to fill with the liquid 12 which proceeds from the medication reservoir 2 into the gap 30 at that location at which the gap 30 is in contact with the liquid 12.

Air bubbles having a diameter smaller than the gap width s can pass the gap 30 unimpeded. In order that such air bubbles only amount to a fraction $k_2$ of the conveying volume V of the pump 5 in a pump action, the following dimensioning rule is selected for the gap width s:

$$s \leq (6 \cdot k_2 \cdot V/\pi)^{\frac{1}{3}} \tag{3}$$

Given the following, assumed parameter values and selected factors:
$Q_{max} = 2.2 \cdot 10^{-6}$ m$^3$/s
$V = 10^{-9}$ m$^3$
$\sigma = 0.06$ N/m
$\eta = 0.7 \cdot 10^{-3}$ Ns/m$^2$
$\alpha = 0^0$
$k_1 = 2$
$k_2 = 10^{-3}$
the dimensioning rules (1), (2) and (3) are satisfied, for example, by the following dimensioning of the gap 30:

$$l \geq 2 \cdot 10^{-2} \text{m}, s = 10^{-4} \text{ and } d = 10^{-3} \text{ m}.$$

It is impossible given this dimensioning of the gap 30 for air to pass the gap 30 as long as the gap 30 merely has contact with the liquid 12 at some location. Only microscopically small air bubbles having a diameter of less than $10^{-4}$ m and a volume of less than 1/1000 of the conveying volume V in a pump action can pass the gap 30. When the gap 30 is completely covered by the air bubble 31, a capillary pressure of $\Delta P_1 = 1200$ Pa arises, this being a negligibly slight pressure drop in comparison to the suction pressure that can be generated by the pump 5. The pump 5 therefore does not stand still but pumps air through the filter 26 until the gap 30 again comes into contact with the liquid 12.

The further filter 27 is provided for that case wherein small air bubbles having a diameter smaller than the gap width s are also to be retained. Given an overall diameter of the further filter 27 of $10^{-2}$ m, a thickness of $150 \cdot 10^{-6}$ m, a pore diameter of $10^{-5}$ m and a 13% proportion of the pores in the overall area of the further filter 27, a minimum pressure difference $\Delta P_{max} = 2.4 \cdot 10^4$ Pa is required in order to be able to pump an air bubble completely covering the further filter 27 through this further filter 27. A value of $7.3 \cdot 10^3$ Pa is derived for the pressure drop across the further filter 27 produced by the maximum liquid flow $Q_{max}$.

When the further filter 27 is completely covered with air, two things can occur. Assuming that, given a pressure $P_R$ in the medication reservoir 2 and given a vapor pressure $P_V$ of the liquid 12, the pump 5 is in the position to generate a suction pressure that achieves the vapor pressure $P_v$, then the air is pumped through the further filter 27 when $P_R - P_V > \Delta P_{max}$.

When, by contrast, $P_R - P_V < \Delta P_{max}$ is valid or when the suction pressure generated by the pump 5 is not adequate for overcoming the pressure difference $\Delta P_{max}$, neither liquid nor air is pumped through the further filter 27, so the pump 5 merely produces cavitations or stands still.

In the illustrated exemplary embodiment, the pressure $P_R$ in the medication reservoir 2 amounts to approximately $7 \cdot 10^4$ Pa and the vapor pressure $P_V$ of the liquid 12 amounts to approximately $6.3 \cdot 10^3$ Pa. This leads to the fact that, given a complete coverage of the further filter 27 with air, the pump does not stand still but pumps air through the further filter 27.

Other gap shapes can also be provided instead of the illustrated annular gap 30, when an optimally large longitudinal extent of the gap is desirable in order to prevent a full coverage of the gap with an air bubble to the greatest extent, in addition to achieving an optimally large gap volume. For example, the gap can proceed in elongated fashion transversely across the convex inside wall 8 of the medication reservoir 2.

Even through the filter having the gap opening has particular advantages in conjunction with an intermittently energized pump, such a filter, of course, can also be employed together with pumps that generate a continuous liquid flow. For such uses, it is particularly the low risk of being plugged by particles or precipitates of the liquid and the slight dependency of the flow resistance in comparison to pore or mesh filters given the formation of surface coats that prove advantageous.

Although modifications and changes may be suggested by those skilled in the art, it is the intention of the inventor to embody within the patent warranted hereon all changes and modifications as reasonably and properly come within the scope of his contribution to the art.

I claim as my invention:

1. A device comprising:
 a liquid source containing liquid;
 intermittently energizable pump means for drawing liquid to be conveyed from said liquid source to an input of said pump means, said pump means having a pump action causing a substantially fixed amount of said liquid to be drawn in a conveying direction from said liquid source; and
 filter means, connected between said liquid source and said input of said pump means, dimensioned for preventing air bubbles having a larger diameter than a predetermined minimum diameter from freely passing through said filter means and for requiring a pressure needed for conveying through said filter means an air bubble, said air bubble having a larger diameter than said prescribed minimum diameter, said pressure being greater than a maximum pressure drop produced in a pump action by said liquid flowing through said filter means, and said filter means having an admission opening formed by a gap having a length in a direction substantially transverse to said conveying direction giving said gap a volume which is greater than said substantially fixed amount.

2. A device as claimed in claim 1 wherein said gap is formed by spaced gap walls and wherein said filter consists of material, at least in said gap walls and in a region surrounding said gap, wettable by said liquid.

3. A device as claimed in claim 1 further comprising: a wetting agent added to said liquid.

4. A device as claimed in claim 1 wherein said gap comprises an annular gap.

5. A device as claimed in claim 1 wherein said filter means has side facing away from said pump shaped for preventing an air bubble from assuming a stable equilibrium position in the region of said filter means.

6. A device as claimed in claim 5 wherein said side has a convex shape.

7. A device as claimed in claim 1 wherein said liquid source comprises a reservoir, and wherein said reservoir has an inside wall shaped for preventing an air bubble from assuming a stable equilibrium position in the region of said filter means.

8. A device as claimed in claim 7 wherein said inside wall has a convex shape.

9. A device as claimed in claim 1 wherein said filter means has a side facing away from said pump means shaped for preventing an air bubble from assuming a stable equilibrium position in the region of said filter means, and wherein said liquid source comprises a reservoir having an inside wall shaped for preventing an air bubble from assuming a stable equilibrium position in the region of said filter means.

10. A device as claimed in claim 9 wherein said side of said filter means and said inside wall of said reservoir both have a convex shape.

11. A device as claimed in claim 1 wherein said pump means comprises a reciprocating pump having a piston capacity substantially free of dead space.

12. A device as claimed in claim 1 further comprising:
 a pore filter disposed between said filter means and said input of said pump, said pore filter having pores therein with a pore width which is smaller than a width of said gap in said filter means.

13. A device as claimed in claim 1 further comprising:
 a mesh filter disposed between said filter means and said input of said pump, said mesh filter having meshes therein with a mesh width which is smaller than a width of said gap in said filter means.

14. A device as claimed in claim 1 further comprising monitoring means for detecting air bubbles in said liquid and for generating an alarm upon the detection of air bubbles in said liquid.

15. A device as claimed in claim 1 further comprising means for monitoring the operation of said pumping means and for generating an alarm upon the detection of a deviation of said operation of said pumping means from a specified value.

16. A device comprising:
a liquid source containing liquid;
intermittently energizable pump means for drawing liquid from said liquid source, said pump means having an input and a pumping action which draws a substantially fixed amount of said liquid from said source to said input in a conveying direction; and
filter means, disposed between said liquid source and said input of said pump, dimensioned for preventing air bubbles from freely passing through said filter means having a larger diameter than a predetermined minimum diameter and for requiring a pressure needed for conveying through said filter means an air bubble, said air bubble having a larger diameter than said predetermined minimum, said pressure being greater than a maximum pressure drop produced in a pump action by said liquid flow through said filter means, said filter means having a housing with an annular opening through which said liquid is conveyed, and a disk disposed in said opening forming a gap between said housing and said disk, said gap having a length in a direction substantially transverse to said conveying direction giving said gap a volume which is greater than said substantially fixed amount.

17. A device as claimed in claim 16 wherein said filter means has a side facing away from said input of said pump means and wherein said liquid source comprises a reservoir having an interior wall, and wherein each of said side of said filter means and said interior wall of said reservoir has a shape for preventing an air bubble from assuming a stable equilibrium position in the region of said filter means.

18. A device as claimed in claim 17 wherein each of said side of said filter means and said interior wall has a convex shape.

19. A device as claimed in claim 16 wherein said filter means has a side facing away from said input of said pump means and wherein said side of said filter means has a shape for preventing an air bubble from assuming a stable equilibrium position in the region of said filter means.

20. A device as claimed in claim 19 wherein said side of said filter has a convex shape.

21. A device as claimed in claim 16 wherein said liquid source comprises a reservoir having an interior wall, and wherein said interior wall of said reservoir has a shape for preventing an air bubble from assuming a stable equilibrium position in the region of said filter means.

22. A device as claimed in claim 21 wherein said interior wall of said reservoir has a convex shape.

23. An implantable infusion apparatus comprising:
a reservoir containing liquid medication;
intermittently energizable pumping means for drawing a substantially fixed dose of said medication in a conveying direction from said reservoir to said input of said pumping means;
filter means, disposed between said reservoir and said input of said pumping means, dimensioned for preventing air bubbles having a diameter larger than a predetermined minimum diameter from freely passing through said filter means and for requiring a pressure needed for conveying through said filter means an air bubble, said air bubble having a diameter larger than said predetermined minimum diameter, said pressure being greater than a maximum pressure drop produced in a pump action by said medication through said filter means, said filter means having a housing with an annular opening therein through which said medication is conveyed, and a disk disposed in said opening forming an annular gap in combination with said housing, said gap having a length in a direction substantially transverse to said conveying direction providing said gap with a volume which is greater than said substantially fixed dose.

24. An infusion apparatus device as claimed in claim 23 further comprising:
a filter disposed between said filter means and said input of said pumping means, said filter having a plurality of openings therein each being smaller than a width of said gap of said filter means.

25. An infusion apparatus as claimed in claim 24 wherein said filter is composed of a material wettable by said liquid medication.

* * * * *